United States Patent
Du et al.

(10) Patent No.: US 11,602,324 B2
(45) Date of Patent: Mar. 14, 2023

(54) FLOW IMAGING PROCESSING METHOD AND ULTRASOUND IMAGING DEVICE

(71) Applicant: SHENZHEN MINDRAY BIO-MEDICAL ELECTRONICS CO., LTD., Guangdong (CN)

(72) Inventors: Yigang Du, Shenzhen (CN); Wei Fan, Shenzhen (CN); Lanxi Xiang, Shenzhen (CN); Yuan Wang, Shenzhen (CN); Yingying Shen, Shenzhen (CN); Kai Wang, Shenzhen (CN); Donghai Qin, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 59 days.

(21) Appl. No.: 17/038,468

(22) Filed: Sep. 30, 2020

(65) Prior Publication Data

US 2021/0007706 A1     Jan. 14, 2021

Related U.S. Application Data

(63) Continuation of application No. PCT/CN2018/081598, filed on Apr. 2, 2018.

(30) Foreign Application Priority Data

Mar. 30, 2018  (WO) ............... PCT/CN2018/081366

(51) Int. Cl.
*A61B 8/06* (2006.01)
*A61B 8/00* (2006.01)
*A61B 8/08* (2006.01)

(52) U.S. Cl.
CPC ............ *A61B 8/06* (2013.01); *A61B 8/461* (2013.01); *A61B 8/5215* (2013.01)

(58) Field of Classification Search
CPC ......... A61B 8/06; A61B 8/461; A61B 8/5215; A61B 8/488; A61B 8/5207; G01S 15/8984; G01S 15/8986
See application file for complete search history.

(56) References Cited

U.S. PATENT DOCUMENTS

| 10,980,517 B2 * | 4/2021 | Park ................... A61B 8/4254 |
| 2014/0276072 A1 * | 9/2014 | Martins ................ A61B 8/463 |
| | | 600/454 |

(Continued)

FOREIGN PATENT DOCUMENTS

| CN | 101856242 A | 10/2010 |
| CN | 101884551 A | 11/2010 |

(Continued)

OTHER PUBLICATIONS

PCT International Search Report and the Written Opinion dated Dec. 12, 2018, issued in related International Application No. PCT/CN2018/081598, with English translation (12 pages).

(Continued)

*Primary Examiner* — Rochelle D Turchen
(74) *Attorney, Agent, or Firm* — Sheppard Mullin Richter & Hampton LLP

(57) ABSTRACT

Embodiments of the present disclosure provide a flow imaging processing method, which may include determining flow imaging parameters, where the flow imaging parameters include a sound speed for calculation, a center frequency of the transmitting pulse for exciting a probe and a imaging depth; obtaining a velocity measurement range; and determining the first target number of the different transmit angles according to the sound speed for calculation, the center frequency of the transmitting pulse, the imaging (Continued)

depth and the velocity measurement range. The embodiments of the present disclosure also provide an ultrasound imaging device.

20 Claims, 4 Drawing Sheets

(56) References Cited

U.S. PATENT DOCUMENTS

| | | |
|---|---|---|
| 2015/0141832 A1 | 5/2015 | Yu et al. |
| 2018/0146952 A1 | 5/2018 | Du et al. |
| 2020/0121289 A1 | 4/2020 | Tian |

FOREIGN PATENT DOCUMENTS

| | | | |
|---|---|---|---|
| CN | 105615919 A | 6/2016 | |
| CN | 105919624 A | 9/2016 | |
| CN | 106102587 A | 11/2016 | |
| CN | 106137257 A | 11/2016 | |
| CN | 106456118 A | 2/2017 | |
| CN | 106580372 A | 4/2017 | |
| WO | WO-0068678 A1 * | 11/2000 | .............. G01P 13/02 |

OTHER PUBLICATIONS

PCT International Preliminary Report on Patentability dated Oct. 15, 2020, issued in related International Application No. PCT/CN2018/081598, with English translation (10 pages).

First Search dated Apr. 25, 2022, issued in related Chinese Application No. 201880058059.2 (3 pages).

First Office Action dated May 5, 2022, issued in related Chinese Application No. 201880058059.2, with English machine translation (30 pages).

Wang Daoyi et al., "Principles of Pulsed Ultrasonic Doppler Diagnosis Technology (II), Pulse Repetition Frequency and Blood Flow Velocity", 1994, pp. 208-212.

* cited by examiner

FLOW IMAGING PROCESSING METHOD AND ULTRASOUND IMAGING DEVICE

CROSS-REFERENCE TO RELATED APPLICATION

This application is a continuation application of International Patent Application No. PCT/CN2018/081598, filed with the China National Intellectual Property Administration (CNIPA) on Apr. 2, 2018, and entitled "BLOOD FLOW MAPPING PROCESSING METHOD AND ULTRASONIC IMAGING DEVICE," which is based on and claims priority to and benefit of International Patent Application No. PCT/CN2018/081366, filed on Mar. 30, 2018. The entire contents of all of the above-identified applications are incorporated herein by reference.

TECHNICAL FIELD

The present disclosure relates to medical imaging, in particular to a processing method for flow imaging and an ultrasound imaging device.

BACKGROUND

Ultrasound vector flow imaging technology has been greatly developed in the past ten years. From academic research to product realization, commercialized medical vector flow imaging has now been realized. For vector flow imaging realized by multi-angle transmitting and/or receiving, the main drawback is that it is prone to aliasing. The final magnitude and direction of the velocity of the flow are obtained by synthesizing components in multiple different angles. Therefore, as long as the aliasing occurs in one angle, the magnitude and direction of the resultant synthesized velocity will have serious deviations.

Currently, in order to reduce the possibility of aliasing, for the vector flow imaging realized by multi-angle transmitting and/or receiving, the pulse repetition frequency (PRF) of the transmitting pulses can be directly increased, or the number of transmitting angles can be reduced to indirectly increase the PRF in the same angle, so as to achieve the purpose of reducing aliasing.

For the vector flow imaging realized by multi-angle transmitting and/or receiving, in the case where there is no aliasing, the more the transmitting angle, the higher the accuracy of the synthesized velocity. However, the PRF will decrease as the angle increases, which makes the aliasing more likely to occur. Once there is aliasing, transmitting in more angles will not only not improve the calculation accuracy of the velocity, but also cause obvious errors in the final synthesized velocity.

SUMMARY

The embodiments of the present disclosure provide processing methods for flow imaging and ultrasound imaging devices, which can generate the first target numbers of transmitting angles, so that the user can enter the vector flow imaging mode according to the first target numbers of transmitting angles so as to obtain a high-precision flow image with reduced aliasing.

In one embodiment, a processing method for flow imaging is provided, which may include:
determining flow imaging parameters, where the flow imaging parameters may include a sound speed for calculation in the flow imaging, a center frequency of a transmitting pulse for exciting a probe and an imaging depth;
obtaining a velocity measurement range; and
determining a first target number of different transmitting angles according to the sound speed for calculation in the flow imaging, the center frequency of the transmitting pulse for exciting the probe, the imaging depth and the velocity measurement range.

In one embodiment, a processing method for flow imaging is provided, which may include:
determining flow imaging parameters, where the flow imaging parameters may include a sound speed for calculation in the flow imaging, a center frequency of a transmitting pulse for exciting a probe and an imaging depth;
obtaining a velocity measurement range; and
determining a range of a number of different transmitting angles according to the sound speed for calculation in the flow imaging, the center frequency of the transmitting pulse for exciting the probe, the imaging depth and the velocity measurement range.

In one embodiment, a processing method for flow imaging is provided, which may include:
determining flow imaging parameters, where the flow imaging parameters may include a sound speed for calculation in the flow imaging, a center frequency of a transmitting pulse for exciting a probe and an imaging depth;
obtaining a first target number of different transmitting angles;
determining a velocity measurement range according to the sound speed for calculation in the flow imaging, the center frequency of the transmitting pulse for exciting the probe, the imaging depth and the first target number of the different transmitting angles.

In one embodiment, an ultrasound imaging device is provided, which may include:
a probe;
a transmitting circuit which may be configured to excite the probe to transmit ultrasound waves to a target object;
a receiving circuit which may be configured to control the probe to receive ultrasound echoes returned from the target object to obtain ultrasound echo signals;
a processor which may be configured to process the ultrasound echo signals to obtain a flow image of the target object; and
a display which may be configured to display the flow image;
where the processor may be further configured to:
determine flow imaging parameters, where the flow imaging parameters may include a sound speed for calculation in the flow imaging, a center frequency of a transmitting pulse for exciting a probe and an imaging depth;
obtain a velocity measurement range; and
determine a first target number of different transmitting angles according to the sound speed for calculation in the flow imaging, the center frequency of the transmitting pulse for exciting the probe, the imaging depth and the velocity measurement range.

In one embodiment, an ultrasound imaging device is provided, which may include:
a probe;
a transmitting circuit which may be configured to excite the probe to transmit ultrasound waves to a target object;
a receiving circuit which may be configured to control the probe to receive ultrasound echoes returned from the target object to obtain ultrasound echo signals;

a processor which may be configured to process the ultrasound echo signals to obtain a flow image of the target object; and a display which may be configured to display the flow image;

where the processor may be further configured to:

determine flow imaging parameters, where the flow imaging parameters may include a sound speed for calculation in the flow imaging, a center frequency of a transmitting pulse for exciting a probe and an imaging depth;

obtain a velocity measurement range; and determine a range of a number of different transmitting angles according to the sound speed for calculation in the flow imaging, the center frequency of the transmitting pulse for exciting the probe, the imaging depth and the velocity measurement range.

In one embodiment, an ultrasound imaging device is provided, which may include:

a probe;

a transmitting circuit which may be configured to excite the probe to transmit ultrasound waves to a target object;

a receiving circuit which may be configured to control the probe to receive ultrasound echoes returned from the target object to obtain ultrasound echo signals;

a processor which may be configured to process the ultrasound echo signals to obtain a flow image of the target object; and a display which may be configured to display the flow image;

where the processor may be further configured to:

determine flow imaging parameters, where the flow imaging parameters may include a sound speed for calculation in the flow imaging, a center frequency of a transmitting pulse for exciting a probe and an imaging depth;

obtain a first target number of different transmitting angles;

determine a velocity measurement range according to the sound speed for calculation in the flow imaging, the center frequency of the transmitting pulse for exciting the probe, the imaging depth and the first target number of the different transmitting angles.

In the technical solutions provided by the embodiments of the present disclosure, a processing method for flow imaging is provided, in which the flow imaging parameters may be determined first. The flow imaging parameters may include the sound speed for calculation in the flow imaging, the center frequency of the transmitting pulse for exciting the probe and the imaging depth. Thereafter, the velocity measurement range imaging may be obtained, and the first target number of transmitting angles may be determined according to the sound speed for calculation in the flow imaging, the center frequency of the transmitting pulse for exciting the probe, the imaging depth and the velocity measurement range. This way, using the flow imaging parameters and the velocity measurement range, the first target number of the transmitting angles can be generated, so that the user can enter the vector flow imaging mode according to the indication of the first target number of the transmitting angles so as to obtain a high-precision flow image with reduced aliasing.

DETAILED DESCRIPTION

The technical solutions in the embodiments of the present disclosure will be clearly and completely described below in connection with the drawings in the embodiments. Obviously, the described embodiments are only a part, but not all, of the embodiments of the present disclosure.

The terms "first", "second", "third", "fourth", etc. (if any) in the specification, the claims and the drawings of the present disclosure are used to distinguish similar objects, but not to describe a specific order or sequence. It should be understood that the data used in this way can be interchanged under appropriate circumstances such that the embodiments described herein can be implemented in an order other than that illustrated or described herein. In addition, the terms "including" and "having" and any variations thereof are intended to mean non-exclusive inclusions. For example, a process, method, system, product or device that includes a series of steps or units will not be necessarily limited to the clearly listed steps or units, but may include other steps or units that are not clearly listed or are inherent to the process, method, product or device.

Figure 1:
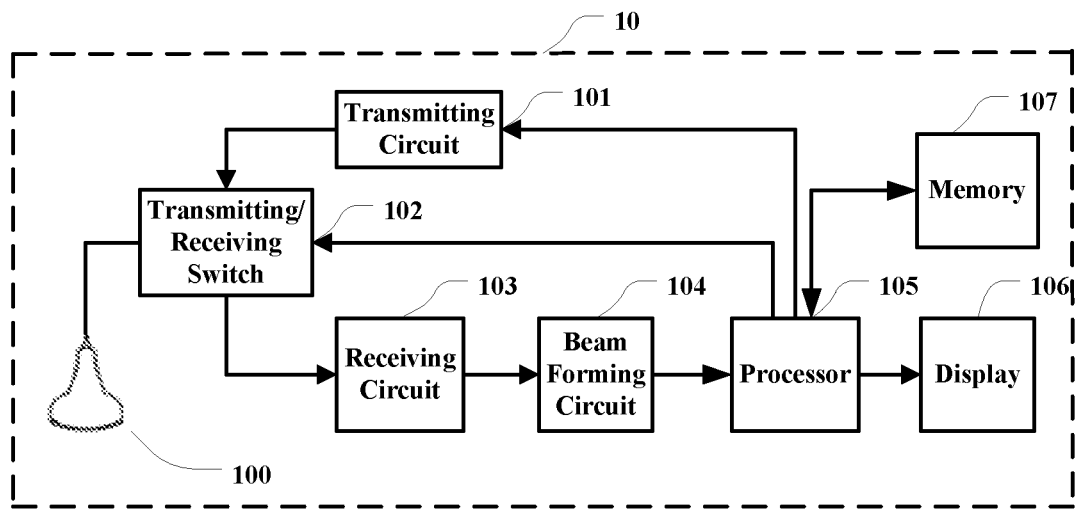
FIG. 1 is a schematic block diagram of an ultrasound imaging device in one embodiment of the present disclosure.

FIG. 1 is a schematic block diagram of an ultrasound imaging device 10 in one embodiment of the present disclosure. The ultrasound imaging device 10 may include a probe 100, a transmitting circuit 101, a transmitting/receiving switch 102, a receiving circuit 103, a beam forming circuit 104, a processor 105 and a display 106. The transmitting circuit 101 may excite the probe 100 to transmit ultrasound waves to a target object. The receiving circuit 103 may receive the ultrasound echoes returned from the target object through the probe 100 to obtain the ultrasound echo signals. The ultrasound echo signal may be sent to the processor 105 after being beam-formed by the beam forming circuit 104. The processor 105 may process the ultrasound echo signals to obtain a flow image of the target object. The flow image obtained by the processor 105 may be stored in a memory 107. These flow images may be displayed on the display 106.

In the embodiments of the present disclosure, the display 106 of the ultrasound imaging device 10 may be a touch screen, a liquid crystal display screen, etc., or may be an independent display device such as a liquid crystal display or a TV, etc. which is independent of the ultrasound imaging device 10. The display 106 may also be the display screen in an electronic device such as a mobile phone, a tablet computer or the like.

In the embodiments of the present disclosure, the memory 107 of the ultrasound imaging device 10 may be a flash memory card, a solid-state memory, a hard disk, or the like.

In one embodiment of the present disclosure, a computer-readable storage medium may also be provided. The computer-readable storage medium may store a plurality of program instructions. After be called and executed by the processor 105, the plurality of program instructions may perform a part or all of, or any combination of, the steps in the methods of the embodiments of the present disclosure.

In one embodiment, the computer-readable storage medium may be the memory 107, which may be a non-volatile storage medium such as a flash memory card, a solid state memory, a hard disk, or the like.

In the embodiments of the present disclosure, the processor 105 of the ultrasound imaging device 10 may be implemented by software, hardware, firmware, or a combination thereof. The processor 105 may use circuits, single or multiple application specific integrated circuits (ASIC), single or multiple general integrated circuits, single or multiple microprocessors, single or multiple programmable logic devices, or a combination of the foregoing circuits or devices, or other suitable circuits or devices, such that the processor 105 can perform the steps in the imaging methods in the embodiments of the present disclosure.

Hereinafter, three embodiments will be used to describe the processing methods for flow imaging in the present disclosure in detail.

Figure 2:
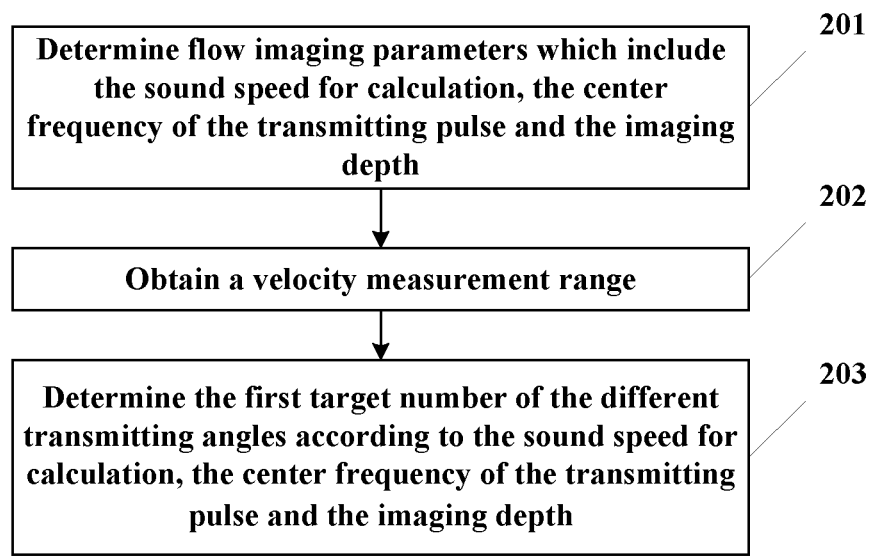
FIG. 2 is a schematic flow chart of a processing method for flow imaging in one embodiment of the present disclosure.

Referring to FIG. 2, in embodiment 1, a processing method for flow imaging may be provided, which may be applied in the ultrasound imaging device 10. The processing method for flow imaging may include the following steps.

In step 201, the flow imaging parameters may be determined. The flow imaging parameters may include the sound speed for calculation in the flow imaging (such as the sound speed to be used in the calculation of the velocity in the flow imaging), the center frequency of the transmitting pulse for exciting the probe and the imaging depth.

In the present embodiment, the ultrasound imaging device 10 may obtain the flow imaging parameters which may include the sound speed for calculation in the flow imaging, the center frequency of the transmitting pulse for exciting the probe and the imaging depth.

In an ultrasound imaging system, the sound speed for calculation in the flow imaging may be determined according to the object to be examined. For different tissues of the human body, the actual sound speed generally varies in a range from 1480 m/s to 1580 m/s. When the object to be examined is determined, the sound speed for calculation in the flow imaging appropriate for the object to be examined may be determined.

The imaging depth may be visible, and generally can be adjusted by the user freely.

The center frequency of the transmitting pulse for exciting the probe may generally be visible, and generally may also be adjusted by the user freely.

In step 202, the velocity measurement range may be obtained.

In the present embodiment, the ultrasound imaging device 10 may further obtain the velocity measurement range thereof. The velocity measurement range cannot exceed the maximum measurable velocity of the ultrasound imaging device 10 when the number of transmitting angle is one.

In step 203, the number of the different transmitting angles to be used in the flow imaging (hereinafter, the "first target number") may be determined according to the sound speed for calculation in the flow imaging, the center frequency of the transmitting pulse for exciting the probe, the imaging depth and the velocity measurement range.

In the present embodiment, the ultrasound imaging device 10 may calculate the first target number of the transmitting angles using the formula below:

$$M \leq c^2 / (8 v_{max} f_0 \times \text{Depth}); \quad (1)$$

Where M represents the first target number of the transmitting angles, c represents the sound speed for calculation in the flow imaging, $v_{max}$ represents the maximum measurable velocity, $f_0$ represents the center frequency of the transmitting pulse for exciting the probe, and Depth represents the imaging depth.

The ultrasound imaging device 10 may intelligently output the first target number of the transmitting angles, that is, the optimal value (which may be the corresponding M value under the conditions of the formula (1), for example, the optimal value here may be the maximum value of M in the formula (1)). The optimal value may be the maximum value of M determined according to the above formula, or a certain value within the range of the maximum value of M.

The number of the transmitting angles may be applied in the vector flow imaging. It may be understood that in practical applications it is also possible that M is equal to 1, which is also suitable for the processing method for flow imaging provided in the present disclosure.

The derivation of formula (1) will be described below in conjunction with specific algorithms and schematic diagrams.

In the processing method for flow imaging provided by the present disclosure, multi-angle transmitting and multi-angle receiving, only multi-angle transmitting or only multi-angle receiving may be used, which will not be limited here. To achieve the flow imaging based on multi-angle transmitting and/or multi-angle receiving, the following calculation methods may be used to calculate flow velocity. Specifically, taking the case where there are 3 different transmitting angles and 3 different receiving angles as an example, the flow velocity may be calculated by the following formula:

$$A \vec{v} = V_D \quad (2)$$

Where $\vec{v}$ represents the final calculated velocity vector, and A and $V_D$ may be represented by the following matrix.

$$A = \begin{bmatrix} \cos\alpha_1 + \cos\beta_1 & \sin\alpha_1 + \sin\beta_1 \\ \cos\alpha_1 + \cos\beta_2 & \sin\alpha_1 + \sin\beta_2 \\ \cos\alpha_1 + \cos\beta_3 & \sin\alpha_1 + \sin\beta_3 \\ \cos\alpha_2 + \cos\beta_1 & \sin\alpha_2 + \sin\beta_1 \\ \cos\alpha_2 + \cos\beta_2 & \sin\alpha_2 + \sin\beta_2 \\ \cos\alpha_2 + \cos\beta_3 & \sin\alpha_2 + \sin\beta_3 \\ \cos\alpha_3 + \cos\beta_1 & \sin\alpha_3 + \sin\beta_1 \\ \cos\alpha_3 + \cos\beta_2 & \sin\alpha_3 + \sin\beta_2 \\ \cos\alpha_3 + \cos\beta_3 & \sin\alpha_3 + \sin\beta_3 \end{bmatrix} \quad (3)$$

In the matrix A, the subscripts 1, 2 and 3 may indicate the first transmitting or receiving angle, the second transmitting or receiving angle and the third transmitting or receiving angle. α may represent the transmitting angle, and β may represent the receiving angle.

In the case that the transmitting angles are the same or the receiving angles are the same, the matrix A may be expressed as:

$$A = \begin{bmatrix} \cos\alpha + \cos\beta_1 & \sin\alpha + \sin\beta_1 \\ \cos\alpha + \cos\beta_2 & \sin\alpha + \sin\beta_2 \\ \cos\alpha + \cos\beta_3 & \sin\alpha + \sin\beta_3 \end{bmatrix} \quad (3.1)$$

where the formula (3.1) indicates that the three receiving angles are different while the transmitting angles α are the same; and $$A = \begin{bmatrix} \cos\alpha_1 + \cos\beta & \sin\alpha_1 + \sin\beta \\ \cos\alpha_2 + \cos\beta & \sin\alpha_2 + \sin\beta \\ \cos\alpha_3 + \cos\beta & \sin\alpha_3 + \sin\beta \end{bmatrix} \quad (3.2)$$

where the formula (3.2) indicates that the three transmitting angles are different while the receiving angles β are the same.

$V_D$ may be expressed as:

$$V_D = \begin{bmatrix} v_{11} \\ v_{12} \\ v_{13} \\ v_{21} \\ v_{22} \\ v_{23} \\ v_{31} \\ v_{32} \\ v_{33} \end{bmatrix} \quad (4)$$

In the matrix $V_D$, $v_{11}$, $v_{12}$, ... $v_{33}$ may represent the flow velocity components corresponding to the transmitting angles calculated according to the traditional Doppler principle. The first number in the subscript is the label of the transmitting angle and the second number in the subscript is the label of the receiving angle. In the case that the transmitting angles are the same or the receiving angles are the same, the matrix $V_D$ may be directly expressed as:

$$V_D = \begin{bmatrix} v_1 \\ v_2 \\ v_3 \end{bmatrix} \quad (4.1)$$

Where the formula (4.1) may be used as an expression when the three receiving angles are different while the transmitting angles α are the same, and may also be used as an expression when the three transmitting angles are different while the receiving angles β are the same.

The solution of the formula (2) regarding the velocity vector $\vec{v}$ may be expressed as:

$$\vec{v} = \begin{bmatrix} v_z \\ v_x \end{bmatrix} = (A^T A)^{-1} A^T V_D \quad (5)$$

Figure 3:
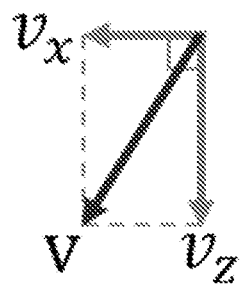
FIG. 3 is a schematic diagram of vector velocity synthesis in one embodiment of the present disclosure.

In the formula (5), $v_z$ and $v_x$ are the calculated velocity components in the imaging depth direction and the image transverse direction, respectively. The two directions are perpendicular to each other. As shown in FIG. 3, the velocity components may be synthesized to obtain the magnitude and direction of the flow velocity.

The number of the transmitting angles may be determined based on two factors during user operation. The two factors may be imaging depth and maximum measurable velocity, which may both be given by the user. The imaging depth may include the imaging depth of the flow imaging and the imaging depth of the current two-dimensional grayscale image.

Figure 4:
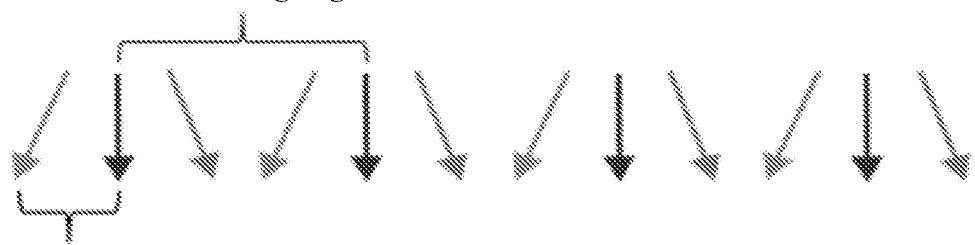
FIG. 4 is a schematic diagram of the alternate transmitting in multiple transmitting angles in one embodiment of the present disclosure.

FIG. 4 is a schematic diagram of the alternate transmitting in multiple transmitting angles (three transmitting angles are shown in the figure, which are merely illustrative) in one embodiment of the present disclosure. As shown in FIG. 4, the imaging depth of the flow imaging may determine the maximum PRF (MaxPRF) of the flow imaging, i.e. the minimum time interval between two adjacent transmitting. Since the transmitting in multiple different transmitting angles are performed alternately, the PRF in the same transmitting angle (LowPRF) cannot exceed MaxPRF divided by the number of the transmitting angles, that is $$\text{LowPRF} \leq \text{MaxPRF}/M; \quad (6)$$

In the formula (6), M represents the number of the transmitting angles. For example, in the embodiments shown in FIG. 4 in which there are three different transmitting angles, the maximum PRF in the same transmitting angle is MaxPRF/3. For the PRF in the same angle, LowPRF is the final effective PRF (that is, the PRF in the same transmitting angle). LowPRF may be used to calculate the flow velocity. The velocity component in each corresponding angle may be calculated by the traditional Doppler method. The specific calculation formula may be as follows:

$$v_{mn} = -\frac{cf_{PRF}}{4\pi f_0} \arctan\left(\frac{\{\Im R(1)\}}{\{\Re R(1)\}}\right) \quad (7)$$

$$R(1) = \frac{1}{K-1} \sum_{i=0}^{K-2} x(i)x(i+1) + y(i)y(i+1) + j[y(i+1)x(i) - x(i+1)y(i)] \quad (8)$$

Where, $v_{mn}$ represents the velocity component in the m-th transmitting angle and the n-th receiving angle calculated through the formula (7) according to the currently designed transmitting and receiving mode, and may correspond to $v_{11}$, $v_{12}$, ... $v_{33}$ or the like according to the transmitting angle and the receiving angle. In the case that there are M transmitting angles and N receiving angles, the elements in the matrices of the formulas (3) and (4) will be arranged in order until the subscripts of the elements are M and N. c represents the sound speed for calculation in the flow imaging, $f_0$ represents the center frequency of the transmitting pulse for exciting the probe, $f_{PRF}$ represents the PRF in the same transmitting angle, that is, the LowPRF mentioned above, K represents the number of transmitting in the same angle when calculating the velocity component, x(i) represents the real part of the signal obtained by the i-th transmitting and corresponding receiving and processing, y(i) represents the imaginary part of the signal obtained by the i-th transmitting and corresponding receiving and processing, $\Im$ is the imaginary part operator, $\Re$ is the real part operator, and j is the imaginary unit, that is, the square of j is −1.

According to the formula (7), the relationship between the maximum measurable velocity in each angle and the corresponding $f_{PRF}$ (i.e. the PRF in the same transmitting angle, LowPRF) may be:

$$v_{max} = \frac{cf_{PRF}}{4f_0}; \quad (9)$$

Combining the formula (9) with the formula (6), we can get:

$$M \leq \text{MaxPRF} \times c/(4v_{max}f_0); \quad (10)$$

Where, MaxPRF is related to the imaging depth. The reciprocal of MaxPRF is the shortest time interval between two adjacent scans, which may be expressed as:

$$1/\text{MaxPRF} = 2 \times \text{Depth}/c \quad (11)$$

Finally, by combining the formula (10) and the formula (11), the formula for calculating the first target number of the transmitting angles may be obtained, namely:

$$M \le c^2/(8v_{max}f_0 \times \text{Depth}).$$

In the technical solutions provided by the embodiments of the present disclosure, a processing method for flow imaging may be provided, in which the flow imaging parameters may be determined first. The flow imaging parameters may include the sound speed for calculation in the flow imaging, the center frequency of the transmitting pulse for exciting the probe and the imaging depth. The flow velocity measurement range may be obtained, and thereafter, the first target number of the transmitting angles may be determined according to the sound speed for calculation in the flow imaging, the center frequency of the transmitting pulse for exciting the probe, the imaging depth and the flow velocity measurement range of the ultrasound imaging device. This way, using the flow imaging parameters and the flow velocity measurement range, the first target number of the transmitting angles can be generated, so that the user can perform the vector flow imaging mode with the first target number of transmitting angles so as to obtain a high-precision flow image with reduced aliasing.

In practical applications, the user can also adjust the center frequency of the transmitting pulse for exciting the probe (for example, change the probe or modify the waveform of the transmitting pulse) or the imaging depth according to the measurement needs, etc. According to the solutions provided by the present disclosure, the first target number of the transmitting angles outputted by the ultrasound imaging device 10 may also change accordingly.

Optionally, based on the embodiments above corresponding to FIG. 2, in one embodiment, after determining the first target number of the transmitting angles according to the sound speed for calculation in the flow imaging, the center frequency of the transmitting pulse for exciting the probe, the imaging depth and the flow velocity measurement range, the method may further include:

obtaining the preset total number of the angles; and determining the number of the different receiving angles to be used in the flow imaging (hereinafter, the "second target number") according to the preset total number of the angles and the first target number of the transmitting angles.

In the present embodiment, after generating the first target number of the different transmitting angles, the ultrasound imaging device 10 may further determine the second target number of the different receiving angles. In one possible embodiment, the user can manually input the second target number of the receiving angles. In another embodiment, a constant may be set in the ultrasound imaging device 10 in advance, which is the second target number of the receiving angles. In practical applications, since the calculation accuracy is mainly determined by the total number of angles which is the number of the transmitting angles multiplied by the number of the receiving angles, a constant may be set in advance as the total number of angles, and the second target number of the receiving angles may be calculated by the device.

The preset total number of angles may be manually set by the user. For example, the preset total number of angles may be 6 or 10, etc., which will not be limited here. Therefore, the second target number of the receiving angles may be obtained according to the calculated first target number of the transmitting angles, as follows:

(1) in the case that the preset total number of angles is 6 and the calculated first target number of the different transmitting angles is 3, the second target number of the different receiving angles is 2;

(2) in the case that the preset total number of angles is 6 and the calculated first target number of the different transmitting angles is 2, the second target number of the different receiving angles is 3;

(3) in the case that the preset total number of angles is 6 and the calculated first target number of the different transmitting angles is 1, the second target number of the different receiving angles is 6;

(4) in the case that the preset total number of angles is 10 and the calculated first target number of the different transmitting angles is 5, the second target number of the different receiving angles is 2;

(5) in the case that the preset total number of angles is 10 and the calculated first target number of the different transmitting angles is 3, the second target number of the different receiving angles is 3.333. It should be noted that since the number of angles should be positive number, the "rounding" method may be used to determine 3.333 as 3. Similarly, in the case that the calculated first target number of the different transmitting angles is 4, the calculated second target number of the different receiving angles will be 2.5. After the rounding, the second number of the different receiving angles will be 3.

In the embodiments of the present disclosure, the ultrasound imaging device 10 may first obtain the preset total number of angles, and then determine the second target number of the different receiving angles according to the preset total number of angles and the first target number of the different transmitting angles. The user may manually set the total number of angles. Alternatively, the imaging device may set a fixed total number of angles. In addition, the user may manually set the second target number of the different receiving angles, or the system may set the second target number of the different receiving angles. The ultrasound imaging device 10 may also calculate the second target number of different receiving angles according to the preset total number of angles and the first target number of the different transmitting angles. The number of the angles can be set through multiples ways, which improve the flexibility and feasibility of the solution.

Optionally, on the basis of the embodiments corresponding to FIG. 2, in one embodiment, the method may further include:

transmitting the ultrasound waves in the first target number of transmitting angles and receiving ultrasound echoes in the second target number of receiving angles to obtain echo data; and generating the flow image according to the echo data.

In the present embodiment, after determining the first target number of the different transmitting angles and the second target number of the different receiving angles, the ultrasound imaging device 10 may control the probe to transmit the ultrasound waves (they may be transmitted alternately, and the sequence of the transmitting in different transmitting angles will not be limited here) to a target object (such as the liver) in the first target number of different transmitting angles (for example, three different transmitting angles, −15°, 0°, 15°, and receive the ultrasound echoes returned from the target object (such as the liver) in the second target number of different receiving angles (for example, three different receiving angles, −15°, 0°, 15° to obtain the echo data, so as to generate the flow image according to the echo data.

It should be noted that the ultrasound waves transmitted by the ultrasound imaging device 10 may include, but not limited to, plane waves, focused waves or divergent waves. The plane wave may refer to the waves whose wave surface (that is, the isophase surface of the waves) is flat when propagating. The focused waves may refer to waves of which all component waves are superimposed with zero phase at a certain fixed point (focus point) in space or time, thereby forming a very high peak at this point. By the analysis of this superposition point, the displacement curve of the wave maker may be obtained. The divergent waves may refer to waves whose anticline-shaped interface is like a convex mirror and has a divergent effect on energy.

In the embodiments of the present disclosure, the ultrasound imaging device 10 may transmit the ultrasound waves in the first target number of different transmitting angles and receive the ultrasound echoes in the second target number of different receiving angles to obtain the echo data, and generate the flow image according to the echo data. This way, according to the current sound speed for calculation in the flow imaging, center frequency of the transmitting pulse for exciting the probe, imaging depth and flow velocity measurement range, reasonable number of the transmitting angles and reasonable number of the receiving angles may be obtained to perform the vector flow imaging. In this way, the possibility of aliasing in the flow imaging can be greatly reduced.

Figure 5:
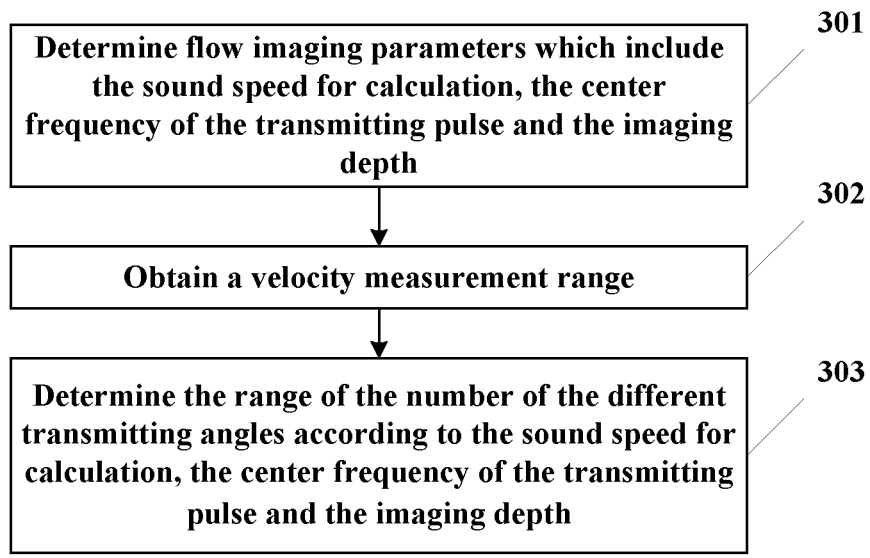
FIG. 5 is a schematic flow chart of a processing method for flow imaging in one embodiment of the present disclosure.

Referring to FIG. 5, in one embodiment, a processing method for flow imaging may be provided, which may be applied to the ultrasound imaging device 10. The method may include the following steps.

In step 301, the flow imaging parameters may be determined. The flow imaging parameters may include the sound speed for calculation in the flow imaging, the center frequency of the transmitting pulse for exciting the probe and the imaging depth.

In the present embodiment, the ultrasound imaging device 10 may obtain the flow imaging parameters which may include the sound speed for calculation in the flow imaging, the center frequency of the transmitting pulse for exciting the probe and the imaging depth.

In an ultrasound imaging system, the sound speed for calculation in the flow imaging may be determined according to the object to be examined. For different tissues of the human body, the actual sound speed generally varies in a range from 1480 m/s to 1580 m/s. When the object to be examined is determined, the sound speed for calculation in the flow imaging appropriate for the object to be examined may be matched.

The imaging depth may be visible, and generally can be adjusted by the user freely.

The center frequency of the transmitting pulse for exciting the probe may generally be visible, and generally can also be adjusted by the user freely.

In step 302, the velocity measurement range of the ultrasound imaging device may be obtained.

In the present embodiment, the ultrasound imaging device 10 may further obtain the velocity measurement range thereof. The velocity measurement range cannot exceed the maximum measurable velocity when the number of transmitting angle is one.

In step 303, the range of the number of different transmitting angles may be determined according to the sound speed for calculation in the flow imaging, the center frequency of the transmitting pulse for exciting the probe, the imaging depth and the velocity measurement range.

In the present embodiment, the ultrasound imaging device 10 may calculate the range of the number of different transmitting angles using the formula below:

$$M \leq c^2/(8v_{max}f_0 \times \text{Depth}); \quad (1)$$

Where M represents the target number in the range of the number of different transmitting angles, c represents the sound speed for calculation in the flow imaging, $v_{max}$ represents the maximum measurable velocity, $f_0$ represents the center frequency of the transmitting pulse for exciting the probe, and Depth represents the imaging depth.

The ultrasound imaging device 10 may intelligently output the range of the number of the different transmitting angles. The user may select a reasonable value from the range of the number of the different transmitting angles according to actual needs as the first target number of the different transmitting angles. The ultrasound imaging device 10 may also automatically output a reasonable value (for example, the maximum value of M in the formula (1)) as the first target number of the different transmitting angles according to the restrictions in the formula (1).

In the present embodiments of the present disclosure, a method for intelligently output the range of the number of transmitting angles may be provided, in which the flow imaging parameters may be determined first. The flow imaging parameters may include the sound speed for calculation in the flow imaging, the center frequency of the transmitting pulse for exciting the probe and the imaging depth. The flow velocity measurement range may be obtained, and thereafter, the range of the number of different transmitting angles may be determined according to the sound speed for calculation in the flow imaging, the center frequency of the transmitting pulse for exciting the probe, the imaging depth and the flow velocity measurement range. This way, using the flow imaging parameters and the flow velocity measurement range, the range of the number of different transmitting angles can be generated, so that the user can perform the vector flow imaging with the first target number of transmitting angles so as to obtain a high-precision flow image with reduced aliasing.

Optionally, based on the embodiments above corresponding to FIG. 5, in one embodiment, the processing method for flow imaging may further include:

determining the first target number of the different transmitting angles from the range of the number of different transmitting angles.

In the present embodiment, the ultrasound imaging device 10 may determine the first target number of the different transmitting angles from the range of the number of different transmitting angles. Specifically, the first target number of the different transmitting angles may be determined in the following two methods.

In the first method, the ultrasound imaging device 10 may actively generate the first target number of the different transmitting angles.

In this method, the ultrasound imaging device 10 may calculate an optimal value according to the calculated range of the number of different transmitting angles (the calculation may be performed by outputting the corresponding M value according to the restrictions of the formula (1), for example, the optimal value here may be the maximum value of M in the formula (1)). For example, in the case that the range of the number of different transmitting angles is 1 to 5, 5 may be selected as the first target number of the different transmitting angles.

In the second method, the ultrasound imaging device 10 may passively generate the first target number of the different transmitting angles.

In this method, after calculating the range of the number of different transmitting angles, the ultrasound imaging device 10 may display the range on the interface of the ultrasound imaging device 10. The user can select a value from the range of the number of different transmitting angles through the interface of the ultrasound imaging device 10 according to actual needs as the first target number of the different transmitting angles.

In the embodiments of the present disclosure, the ultrasound imaging device 10 may determine the first target number of the different transmitting angles from the range of the number of different transmitting angles. In this way, using the flow imaging parameters and the flow velocity measurement range, the first target number of the different transmitting angles may be generated, so that the user can perform the vector flow imaging with the first target number of different transmitting angles so as to obtain a high-precision flow image with reduced aliasing.

Optionally, based on the embodiments above corresponding to FIG. 5, in one embodiment, after determining the range of the number of transmitting angles according to the sound speed for calculation in the flow imaging, the center frequency of the transmitting pulse for exciting the probe, the imaging depth and the flow velocity measurement range, the method may further include:

obtaining the preset total number of the angles; and determining the second target number of the different receiving angles according to the preset total number of the angles and the first target number of the transmitting angles.

In the present embodiment, after generating the first target number of the different transmitting angles, the ultrasound imaging device 10 may further determine the second target number of the different receiving angles. In one possible embodiment, the user can manually input the second target number of the receiving angles. In another embodiment, a constant may be set in the ultrasound imaging device 10 in advance, which is the second target number of the receiving angles. In practical applications, since the calculation accuracy is mainly determined by the total number of angles which is the number of the transmitting angles multiplied by the number of the receiving angles, a constant may be set in advance as the total number of the angles, and the second target number of the receiving angles may be calculated by the device.

The preset total number of the angles may be manually set by the user. For example, the preset total number of angles may be 6 or 10, etc., which will not be limited here. Therefore, the second target number of the receiving angles may be obtained according to the calculated first target number of the transmitting angles, as follows:

(1) in the case that the preset total number of the angles is 6 and the calculated first target number of the different transmitting angles is 3, the second target number of the different receiving angles is 2;

(2) in the case that the preset total number of the angles is 6 and the calculated first target number of the different transmitting angles is 2, the second target number of the different receiving angles is 3;

(3) in the case that the preset total number of the angles is 6 and the calculated first target number of the different transmitting angles is 1, the second target number of the different receiving angles is 6;

(4) in the case that the preset total number of the angles is 10 and the calculated first target number of the different transmitting angles is 5, the second target number of the different receiving angles is 2;

(5) in the case that the preset total number of the angles is 10 and the calculated first target number of the different transmitting angles is 3, the second target number of the different receiving angles is 3.333. It should be noted that since the number of angles should be positive number, the "rounding" method may be used to determine 3.333 as 3. Similarly, in the case that the calculated first target number of the different transmitting angles is 4, the calculated second target number of the different receiving angles will be 2.5. After the rounding, the second number of the different receiving angles will be 3.

In the embodiments of the present disclosure, the ultrasound imaging device 10 may first obtain the preset total number of the angles, and then determine the second target number of the different receiving angles according to the preset total number of angles and the first target number of the different transmitting angles. The user may manually set the total number of angles. Alternatively, the imaging device may set a fixed total number of angles. In addition, the user may manually set the second target number of the different receiving angles, or the system may set the second target number of the different receiving angles. The ultrasound imaging device 10 may also calculate the second target number of different receiving angles according to the preset total number of angles and the first target number of the different transmitting angles. The number of the angles can be set through multiples ways, which improve the flexibility and feasibility of the solution.

Optionally, on the basis of the embodiments corresponding to FIG. 5, in one embodiment, the method may further include:

transmitting the ultrasound waves in the first target number of transmitting angles and receiving ultrasound echoes in the second target number of receiving angles to obtain echo data; and generating the flow image according to the echo data.

In the present embodiment, after determining the first target number of the different transmitting angles and the second target number of the different receiving angles, the ultrasound imaging device 10 may transmit the ultrasound waves to the target object (such as the liver) in the first target number of different transmitting angles and receive the ultrasound echoes returned from the target object (such as the liver) in the second target number of different receiving angles to obtain the echo data, so as to generate the flow image according to the echo data.

It should be noted that the ultrasound waves transmitted by the ultrasound imaging device 10 may include, but not limited to, plane waves, focused waves or divergent waves. The plane wave may refer to the waves whose wave surface (that is, the isophase surface of the waves) is flat when propagating. The focused waves may refer to waves of which all component waves are superimposed with zero phase at a certain fixed point (focus point) in space or time, thereby forming a very high peak at this point. By the analysis of this superposition point, the displacement curve of the wave maker may be obtained. The divergent waves may refer to waves whose anticline-shaped interface is like a convex mirror and has a divergent effect on energy.

In the embodiments of the present disclosure, the ultrasound imaging device 10 may transmit the ultrasound waves in the first target number of different transmitting angles and receive the ultrasound echoes in the second target number of different receiving angles to obtain the echo data, and generate the flow image according to the echo data. This way, according to the current sound speed for calculation in the flow imaging, center frequency of the transmitting pulse for exciting the probe, imaging depth and flow velocity measurement range, reasonable number of the transmitting angles and reasonable number of the receiving angles may be obtained to perform the vector flow imaging. In this way, the possibility of aliasing in the flow imaging can be greatly reduced.

Figure 6:
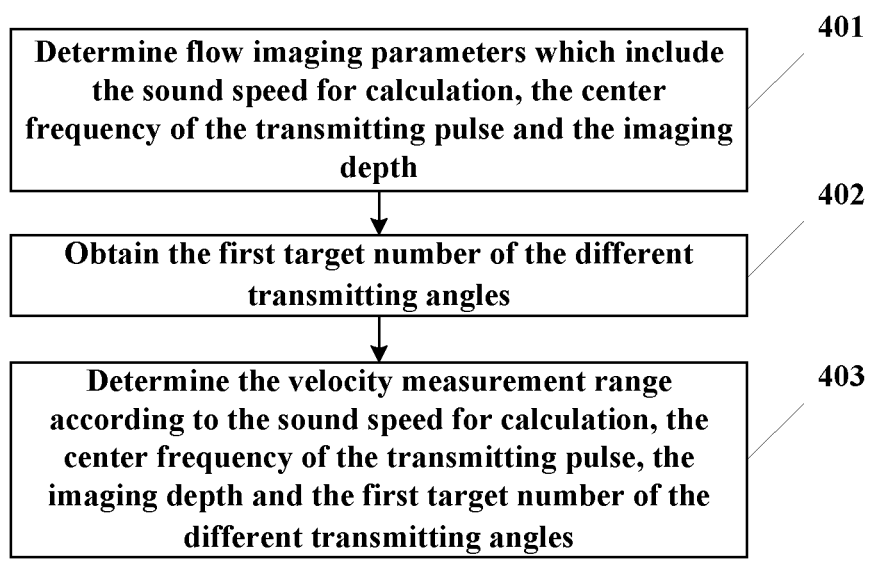
FIG. 6 is a schematic flow chart of a processing method for flow imaging in one embodiment of the present disclosure.
Figure 7:
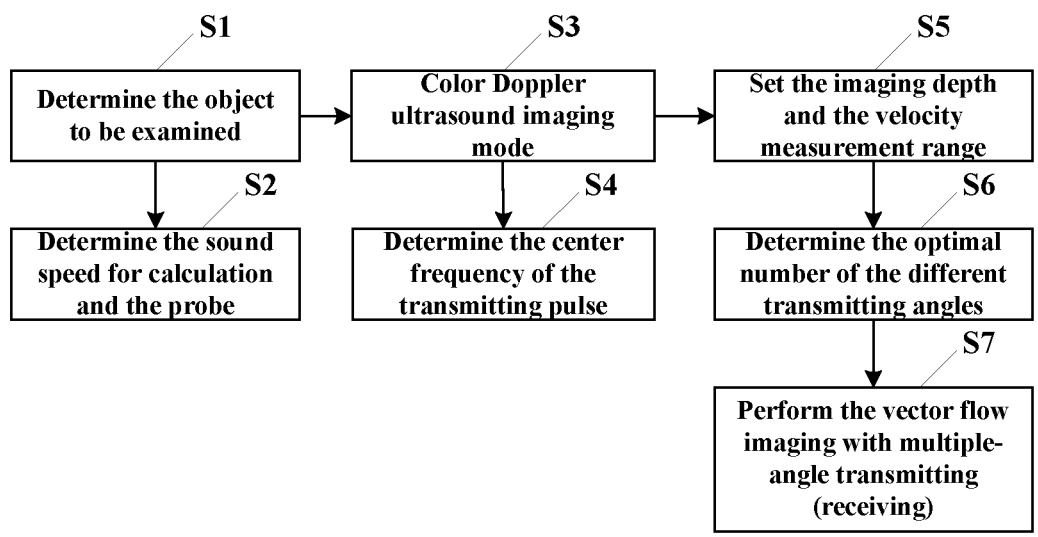
FIG. 7 is a schematic diagram of an operation flow of the flow imaging in one application scenario of the present disclosure.

Referring to FIG. 6, in one embodiment, a processing method for flow imaging may be provided, which may be applied to the ultrasound imaging device 10. The method may include the following steps.

In step 401, the flow imaging parameters may be determined. The flow imaging parameters may include the sound speed for calculation in the flow imaging, the center frequency of the transmitting pulse for exciting the probe and the imaging depth.

In the present embodiment, the ultrasound imaging device 10 may obtain the flow imaging parameters which may include the sound speed for calculation in the flow imaging, the center frequency of the transmitting pulse for exciting the probe and the imaging depth.

In an ultrasound imaging system, the sound speed for calculation in the flow imaging may be determined according to the object to be examined. For different tissues of the human body, the sound speed generally varies in a range from 1480 m/s to 1580 m/s. When the object to be examined is determined, the sound speed for calculation in the flow imaging appropriate for the object to be examined may be according determined.

The imaging depth may be visible, and generally can be adjusted by the user freely.

The center frequency of the transmitting pulse for exciting the probe may generally be visible, and generally can also be adjusted by the user freely.

In step 402, the first target number of the different transmitting angles may be obtained.

In the present embodiment, the ultrasound imaging device 10 may obtain the number of the transmitting angles. The number of the transmitting angles may be set by the user, or may be preset by the ultrasound imaging device 10. Moreover, in the present embodiment, the PRFs in different transmitting angles may be the same.

In step 403, the flow velocity measurement range may be determined according to the sound speed for calculation in the flow imaging, the center frequency of the transmitting pulse for exciting the probe, the imaging depth and the first target number of the transmitting angles.

In this embodiment, the ultrasound imaging device 10 may use the following formula to calculate the measurable velocity of flow:

$$M \leq c^2/(8v_{max}f_0 \times \text{Depth}); \quad (1)$$

Where M represents the number of the transmitting angles, c represents the sound speed for calculation in the flow imaging, $v_{max}$ represents the maximum measurable velocity, $f_0$ represents the center frequency of the transmitting pulse for exciting the probe, and Depth represents the imaging depth.

The flow velocity measurement range may be the maximum range of the flow velocity that is measurable. The output form may be a maximum value or a range, so as to prompt the user the maximum range of the flow velocity that is measurable.

In the present embodiment, the user can adjust the first target number of the different transmitting angles. The flow velocity measurement range may be determined according to the sound speed for calculation in the flow imaging, the center frequency of the transmitting pulse for exciting the probe, the imaging depth and the number of the transmitting angles. The user is allowed to adjust within the velocity measurement range. In this way, the user can make reasonable adjustments to the measurement velocity according to actual needs. On the one hand, the flexibility and feasibility of the measurement are improved; on the other hand, the adjustment of the measurement velocity within the velocity measurement range can reduce the possibility of aliasing in the flow imaging in a more precise condition.

Optionally, based on the embodiments above corresponding to FIG. 6, in one embodiment, after determining the flow velocity measurement range according to the sound speed for calculation in the flow imaging, the center frequency of the transmitting pulse for exciting the probe, the imaging depth and the first target number of the different transmitting angles, the method may further include:

obtaining the preset total number of the angles; and determining the second target number of the different receiving angles according to the preset total number of the angles and the first target number of the transmitting angles.

In the present embodiment, after generating the first target number of the different transmitting angles, the ultrasound imaging device 10 may further determine the second target number of the different receiving angles. In one embodiment, the user may manually input the number of the different receiving angles. In another embodiment, a constant may be set in the ultrasound imaging device 10 in advance, which is the second target number of the receiving angles. In practical applications, since the calculation accuracy is mainly determined by the total number of angles which is the number of the transmitting angles multiplied by the number of the receiving angles, a constant may be set in advance as the total number of the angles, and the number of the receiving angles may be calculated by the device.

The preset total number of angles may be manually set by the user. For example, the preset total number of angles may be 6 or 10, etc., which will not be limited here. Therefore, the second target number of the receiving angles may be obtained according to the calculated first target number of the transmitting angles, as follows:

(1) in the case that the preset total number of the angles is 6 and the calculated first target number of the different transmitting angles is 3, the second target number of the different receiving angles is 2;

(2) in the case that the preset total number of the angles is 6 and the calculated first target number of the different transmitting angles is 2, the second target number of the different receiving angles is 3;

(3) in the case that the preset total number of the angles is 6 and the calculated first target number of the different transmitting angles is 1, the second target number of the different receiving angles is 6;

(4) in the case that the preset total number of the angles is 10 and the calculated first target number of the different transmitting angles is 5, the second target number of the different receiving angles is 2;

(5) in the case that the preset total number of the angles is 10 and the calculated first target number of the different transmitting angles is 3, the second target number of the different receiving angles is 3.333. It should be noted that since the number of angles should be positive number, the "rounding" method may be used to determine 3.333 as 3. Similarly, in the case that the calculated first target number of the different transmitting angles is 4, the calculated second target number of the different receiving angles will be 2.5. After the rounding, the second number of the different receiving angles will be 3.

In the embodiments of the present disclosure, the ultrasound imaging device 10 may first obtain the preset total number of the angles, and then determine the second target number of the different receiving angles according to the preset total number of angles and the first target number of the different transmitting angles. The user may manually set the total number of angles. Alternatively, the imaging device may set a fixed total number of angles. In addition, the user may manually set the second target number of the different receiving angles, or the system may set the second target number of the different receiving angles. The ultrasound imaging device 10 may also calculate the second target number of different receiving angles according to the preset total number of angles and the first target number of the different transmitting angles. The number of the angles can be set through multiples ways, which improve the flexibility and feasibility of the solution.

Optionally, on the basis of the embodiments corresponding to FIG. 6, in one embodiment, the method may further include:

transmitting the ultrasound waves in the first target number of transmitting angles and receiving ultrasound echoes in the second target number of receiving angles to obtain echo data; and generating the flow image according to the echo data.

In the present embodiment, after determining the number of the different transmitting angles and the number of the different receiving angles, the ultrasound imaging device 10 may transmit the ultrasound waves to the target object (such as the liver) in the first target number of different transmitting angles and receive the ultrasound echoes returned from the target object (such as the liver) in the second target number of different receiving angles to obtain the echo data, so as to generate the flow image according to the echo data.

It should be noted that the ultrasound waves transmitted by the ultrasound imaging device 10 may include, but not limited to, plane waves, focused waves or divergent waves. The plane wave may refer to the waves whose wave surface (that is, the isophase surface of the waves) is flat when propagating. The focused waves may refer to waves of which all component waves are superimposed with zero phase at a certain fixed point (focus point) in space or time, thereby forming a very high peak at this point. By the analysis of this superposition point, the displacement curve of the wave maker may be obtained. The divergent waves may refer to waves whose anticline-shaped interface is like a convex mirror and has a divergent effect on energy.

In the embodiments of the present disclosure, the ultrasound imaging device 10 may transmit the ultrasound waves in the first target number of different transmitting angles and receive the ultrasound echoes in the second target number of different receiving angles to obtain the echo data, and generate the flow image according to the echo data. This way, according to the current sound speed for calculation in the flow imaging, center frequency of the transmitting pulse for exciting the probe, imaging depth and flow velocity measurement range, reasonable number of the transmitting angles and reasonable number of the receiving angles may be obtained to perform the vector flow imaging. In this way, the possibility of aliasing in the flow imaging can be greatly reduced.

In order to prevent aliasing and obtain the optimal number of the different transmitting angles, a relatively common operation flow will be illustrated in conjunction with FIG. 10. In practical applications, many other operation modes may also be used. For example, the center frequency of the transmitting pulse for exciting the probe may be reduced as the increase of the maximum measurement velocity, which can increase the number of the transmitting angles and improve the accuracy of vector flow imaging. In addition, the calculation accuracy of the velocity can be improved by increasing the number of the different receiving angles.

FIG. 10 is a schematic diagram of an operation flow of the flow imaging in the application scenario of the present disclosure.

In step S1, the user may determine the object to be examined by the flow imaging, such as the liver, the gallbladder, the stomach or the like.

In step S2, the sound speed for calculation in the flow imaging may be determined according to the object to be examined. For different tissues of the human body, the sound speed generally varies in a range from 1480 m/s to 1580 m/s. When the object to be examined is determined, the sound speed for calculation in the flow imaging appropriate for the object to be examined may be accordingly determined.

In step S3, it may be determined whether there is aliasing in the flow imaging according to the traditional color Doppler ultrasound imaging. After performing the anti-aliasing parameter adjustment, the vector flow imaging mode may be entered while keeping the adjusted parameters to be unchanged.

In step S4, if the aliasing occurs, the center frequency of the transmitting pulse for exciting the probe may be reduced. Specifically, the color Doppler ultrasound imaging mode may be entered first to observe whether there is aliasing. If there is aliasing, the center frequency of the transmitting pulse for exciting the probe may be reduced (adjusting the transmitting waveform or directly replace the probe with a low-frequency probe) to achieve no aliasing or as little aliasing as possible state. Thereafter, the current center frequency of the probe for transmitting signal and the sound speed for calculation in the flow imaging may be maintained.

In step S5, if the aliasing occurs, it may also be possible to reduce the aliasing by increasing the PRF. Specifically, the color Doppler ultrasound imaging mode may be entered first to observe whether there is aliasing. If there is aliasing, the PRF may be adjusted (increased) to achieve no aliasing or as little aliasing as possible state. Thereafter, the current imaging depth and the maximum measurement velocity may be maintained to enter into the vector flow imaging mode.

In step S6, after entering the vector flow imaging mode, the ultrasound imaging device 10 may determine the optimal number of the different transmitting angles (reference may be made to the description above regarding the optimal number) according to the determined center frequency of the transmitting pulse for exciting the probe, sound speed for calculation in the flow imaging, imaging depth, and maximum measurement velocity.

In step S7, after determining the number of the different transmitting angles, the ultrasound imaging device 10 may transmit the ultrasound wave to the object to be examined in the number of different transmitting angles and receive the echo data of the object to be examined in the number of different receiving angles, so as to generate the flow images according to the echo data.

It should be noted that in practical applications, the number of the different transmitting angles may be obtained by adjusting a value directly given by the user according to the center frequency of the transmitting pulse for exciting the probe, the sound speed for calculation in the flow imaging, the imaging depth and the velocity measurement range. Alternatively, the number of the different transmitting angles may be given by the user, and the current maximum imaging depth may be determined according to the sound speed for calculation in the flow imaging, the center frequency of the transmitting pulse for exciting the probe and the maximum measurement velocity. Alternatively, the number of the different transmitting angles may be directly given by the user, and the center frequency of the transmitting pulse for exciting the probe may be determined according to the sound speed for calculation in the flow imaging, the maximum measurement velocity and the current imaging depth.

The number of the transmitting angles may be adjustable. According to the sound speed for calculation in the flow imaging (determined by the examination mode), the center frequency of the transmitting pulse for exciting the probe (adjustable by changing the probe or modifying the transmitting waveform) and the current imaging depth (determined according to the measurement requirements), the maximum measurement velocity (that is, $v_{max}$ in the formula (1) above) may be determined. The user can perform the adjustment in the range of this maximum value).

The embodiments above may be implemented in whole or in part by software, hardware, firmware or any combination thereof. When implemented by software, they may be implemented in the form of a computer program product in whole or in part.

The computer program product may include one or more computer instructions. When the computer instructions are loaded and executed in the computer, the processes or functions described in the embodiments of the present disclosure may be generated in whole or in part. The computer may be a general-purpose computer, a special-purpose computer, a computer network, or other programmable devices. The computer instructions may be stored in a computer-readable storage medium, or be transmitted from one computer-readable storage medium to another computer-readable storage medium. For example, the computer instructions may be transmitted from a website, computer, server or data center to another website, computer, server or data center via wired (such as coaxial cable, optical fiber, Digital Subscriber Line (DSL)) or wireless (such as infrared, wireless, microwave, etc.) connection. The computer-readable storage medium may be any available medium that can be used for storing by a computer or a data storage device such as an integrated server or data center which include one or more available media. The available medium may be a magnetic medium (such as a floppy disk, a hard disk, a magnetic tape), an optical medium (such as a DVD), a semiconductor medium (such as a solid state hard disk (SSD) or the like.

Those skilled in the art can clearly understand that, regarding the specific working process of the system, device and unit described above, reference may be made to the corresponding processes in the methods described above, which, for the convenience and conciseness of the description, will not be repeated here.

It should be understood that in the embodiments of the present disclosure the disclosed systems, devices and methods may be implemented in other ways. For example, the devices described above are only illustrative. For example, the division of the units is only a logical function division, and there may be other divisions in actual implementation. For example, multiple units or components may be combined or be integrated into another system. Some features may be ignored or not implemented. In addition, the displayed or discussed mutual coupling or direct coupling or communication connection may be indirect coupling or communication connection through some interfaces, devices or units, and may be in electrical, mechanical or other forms.

The units described as separate components may or may not be physically separated. The components displayed as units may or may not be physical units, that is, they may be located in one place, or they may be distributed on multiple network units. Some or all of the units may be selected according to actual needs to achieve the objectives of the solutions of the embodiments.

In addition, the functional units in the embodiments of the present disclosure may be integrated into one unit. Alternatively, the units may exist alone physically. Alternatively, two or more units may be integrated into one unit. The integrated unit may be implemented in the form of hardware or software functional unit.

In the case that the integrated unit is implemented in the form of a software functional unit and sold or used as an independent product, it may be stored in a computer readable storage medium. Based on this understanding, the essential part or the part that contributes to the existing technology or all or part of the technical solutions of the present disclosure may be embodied in the form of a software product. The software product may be stored in a storage medium, and may include multiple instructions which may be used to make a computer device (which may be a personal computer, a server, or a network device, etc.) to execute all or part of the steps of the method described in the embodiments of the present disclosure. The storage media may include a U disk, a mobile hard disk, a read-only memory (ROM), a random access memory (RAM), a magnetic disk, an optical disk or other media that can store program code.

As mentioned above, the embodiments above are only used to illustrate, but not limit, the technical solutions of the present disclosure. Although the present disclosure has been described in detail with reference to the embodiments, a person of ordinary skill in the art should understand that the technical solutions of the embodiments may be modified, or some of the technical features may be equivalently replaced, and these modifications or replacements will not cause the essence of the corresponding technical solutions to deviate from the spirit and scope of the technical solutions of the embodiments of the present disclosure.

The invention claimed is:

1. A processing method for flow imaging, comprising:
   determining flow imaging parameters, wherein the flow imaging parameters comprises a sound speed for calculation, a center frequency of a transmitting pulse for exciting a probe and an imaging depth;
   obtaining a velocity measurement range;
   determining a first target number of different transmitting angles according to the sound speed for calculation, the center frequency of the transmitting pulse for exciting the probe, the imaging depth and the velocity measurement range;
   obtaining a preset total number of angles; and
   determining a second target number of different receiving angles according to the preset total number of the angles and the first target number of the different transmitting angles.

2. The method of claim 1, wherein the preset total number is a product of the first target number and the second target number.

3. The method of claim 1, further comprising:
   transmitting ultrasound waves in the first target number of different transmitting angles and receiving ultrasound echoes in the second target number of different receiving angles to obtain echo data; and generating a flow image according to the echo data.

4. A processing method for flow imaging, comprising:

determining flow imaging parameters, wherein the flow imaging parameters comprises a sound speed for calculation, a center frequency of a transmitting pulse for exciting a probe and an imaging depth;

obtaining a velocity measurement range;

determining a range of a number of different transmitting angles according to the sound speed for calculation, the center frequency of the transmitting pulse for exciting the probe, the imaging depth and the velocity measurement range;

determining a first target number of the different transmitting angles from the range of the number of the different transmitting angles;

obtaining a preset total number of angles; and determining a second target number of different receiving angles according to the preset total number of the angles and the first target number of the different transmitting angles.

5. The method of claim 4, wherein the preset total number is a product of the first target number and the second target number.

6. The method of claim 4, wherein the first target number is one.

7. The method of claim 4, further comprising:

transmitting ultrasound waves in the first target number of different transmitting angles and receiving ultrasound echoes in the second target number of different receiving angles to obtain echo data; and generating a flow image according to the echo data.

8. A processing method for flow imaging, comprising:

determining flow imaging parameters, wherein the flow imaging parameters comprises a sound speed for calculation, a center frequency of a transmitting pulse for exciting a probe and an imaging depth;

obtaining a first target number of different transmitting angles;

determining a velocity measurement range according to the sound speed for calculation, the center frequency of the transmitting pulse for exciting the probe, the imaging depth and the first target number of the different transmitting angles;

obtaining a preset total number of angles; and determining a second target number of different receiving angles according to the preset total number of the angles and the first target number of the different transmitting angles.

9. The method of claim 8, wherein the preset total number is a product of the first target number and the second target number.

10. The method of claim 8, further comprising:

transmitting ultrasound waves in the first target number of different transmitting angles and receiving ultrasound echoes in the second target number of different receiving angles to obtain echo data; and generating a flow image according to the echo data.

11. An ultrasound imaging device, comprising a processor and a non-transitory computer-readable storage medium storing instructions that, when executed by the processor, cause the ultrasound imaging device to perform operations comprising:

determining flow imaging parameters, wherein the flow imaging parameters comprises a sound speed for calculation, a center frequency of a transmitting pulse for exciting a probe and an imaging depth;

obtaining a velocity measurement range;

determining a first target number of different transmitting angles according to the sound speed for calculation, the center frequency of the transmitting pulse for exciting the probe, the imaging depth and the velocity measurement range;

obtaining a preset total number of angles; and determining a second target number of different receiving angles according to the preset total number of the angles and the first target number of the different transmitting angles.

12. The ultrasound imaging device of claim 11, wherein the preset total number is a product of the first target number and the second target number.

13. The ultrasound imaging device of claim 11, wherein the operations further comprise:

transmitting ultrasound waves in the first target number of different transmitting angles and receiving ultrasound echoes in the second target number of different receiving angles to obtain echo data; and generating a flow image according to the echo data.

14. An ultrasound imaging device, comprising a processor and a non-transitory computer-readable storage medium storing instructions that, when executed by the processor, cause the ultrasound imaging device to perform operations comprising:

determining flow imaging parameters, wherein the flow imaging parameters comprises a sound speed for calculation, a center frequency of a transmitting pulse for exciting a probe and an imaging depth;

obtaining a velocity measurement range;

determining a range of a number of different transmitting angles according to the sound speed for calculation, the center frequency of the transmitting pulse for exciting the probe, the imaging depth and the velocity measurement range;

determining a first target number of the different transmitting angles from the range of the number of the different transmitting angles;

obtaining a preset total number of angles; and determining a second target number of different receiving angles according to the preset total number of the angles and the first target number of the different transmitting angles.

15. The ultrasound imaging device of claim 14, wherein the preset total number is a product of the first target number and the second target number.

16. The ultrasound imaging device of claim 14, wherein the first target number is one.

17. The ultrasound imaging device of claim 14, wherein the operations further comprise:

transmitting ultrasound waves in the first target number of different transmitting angles and receiving ultrasound echoes in the second target number of different receiving angles to obtain echo data; and generating a flow image according to the echo data.

18. An ultrasound imaging device, comprising a processor and a non-transitory computer-readable storage medium storing instructions that, when executed by the processor, cause the ultrasound imaging device to perform operations comprising:

determining flow imaging parameters, wherein the flow imaging parameters comprises a sound speed for calculation, a center frequency of a transmitting pulse for exciting a probe and an imaging depth;

obtaining a first target number of different transmitting angles;

determining a velocity measurement range according to the sound speed for calculation, the center frequency of the transmitting pulse for exciting the probe, the imaging depth and the first target number of the different transmitting angles;

obtaining a preset total number of angles; and determining a second target number of different receiving angles according to the preset total number of the angles and the first target number of the different transmitting angles.

19. The ultrasound imaging device of claim 18, wherein the preset total number is a product of the first target number and the second target number.

20. The ultrasound imaging device of claim 18, wherein the operations further comprise:

transmitting ultrasound waves in the first target number of different transmitting angles and receiving ultrasound echoes in the second target number of different receiving angles to obtain echo data; and generating a flow image according to the echo data.

\* \* \* \* \*